(12) United States Patent
Davis Moore

(10) Patent No.: US 10,818,380 B1
(45) Date of Patent: Oct. 27, 2020

(54) METHODS FOR IDENTIFYING AND TREATING ERRORS IN BIOCHEMICAL PATHWAYS

(71) Applicant: Amy Kathleen Davis Moore, Chesterfield, MO (US)

(72) Inventor: Amy Kathleen Davis Moore, Chesterfield, MO (US)

(*) Notice: Subject to any disclaimer, the term of this patent is extended or adjusted under 35 U.S.C. 154(b) by 0 days.

(21) Appl. No.: 14/262,733

(22) Filed: Apr. 26, 2014

Related U.S. Application Data

(60) Provisional application No. 61/818,184, filed on May 1, 2013.

(51) Int. Cl.
| | | |
|---|---|---|
| *G01N 33/48* | (2006.01) | |
| *G16H 10/60* | (2018.01) | |
| *A61B 5/00* | (2006.01) | |
| *G06G 7/58* | (2006.01) | |

(52) U.S. Cl.
CPC .......... *G16H 10/60* (2018.01); *A61B 5/4866* (2013.01)

(58) Field of Classification Search
None
See application file for complete search history.

(56) References Cited

U.S. PATENT DOCUMENTS

| | | |
|---|---|---|
| 6,142,927 A | 11/2000 | Clark |
| 8,099,159 B2 | 1/2012 | Cook |
| 8,131,355 B2 | 3/2012 | Clark |

OTHER PUBLICATIONS

Zhang et al., "Genetic Variants in the Folate Pathway and the Risk of Neural Tube Defects: A Meta-Analysis of the Published Literature," PLoS One, vol. 8, Issue 4, Apr. 2013, 11 pages.

Metabolic Pathways, International Union of Biochemistry and Molecular Biology, Sigma Life Science, 22nd Edition, Retrieved online from <https://www.sigmaaldrich.com/content/dam/sigma-aldrich/docs/Sigma/General_information/metabolic_pathways_poster.pdf>, 2003, 1 page.

*Primary Examiner* — Eric S Dejong
(74) *Attorney, Agent, or Firm* — Faegre Drinker Biddle & Reath LLP

(57) ABSTRACT

Disclosed herein are methods, devices and systems of treating dysfunctional biochemical pathway(s) using an individualized treatment plan (ITP) of metabolic support intervention(s) for a patient. The ITP has metabolic support intervention(s) that restore proper functioning of biochemical pathway(s) correcting dysfunction(s) therein. Methods can include determining if the biochemical pathway(s) are dysfunctional by subjecting, via a bio-communication device, the patient to a noninvasive test that includes simulating one or more stimuli that are indicative of the biochemical pathway(s)' s functioning. Methods can include developing the ITP by subjecting, via the bio-communication device, the patient to a noninvasive test that includes simulating metabolic support intervention(s) to identify those that support restoration of proper functioning to the biochemical pathway(s); adding those that support restoration of proper functioning to the biochemical pathway(s); and periodically revising the ITP as re-evaluation of the patient reflects the "then-current" biochemical status of the patient. Methods include implementing the ITP.

13 Claims, 4 Drawing Sheets

| UREA CYCLE MARKERS | | | | |
|---|---|---|---|---|
| | 2SD | Normal | 2SD | Reference Range |
| Ammonia | | 95 | | 25.0 – 88.0 |
| Citrulline | | 104 | | 28-117 |
| Arginine | | | 42 | 35-159 |
| Glycine | | | 1334 | 1058 – 4772 |
| Urea | | | 469 | 223-918 |
| Ornithine | | | 12 | 6-56 |
| Creatinine | 2.3 | | | 3.1 – 19.5 |

FIG. 1

METHODS FOR IDENTIFYING AND TREATING ERRORS IN BIOCHEMICAL PATHWAYS

CROSS REFERENCE TO RELATED APPLICATIONS

This application claims the benefit of U.S. Provisional Patent Application No. 61/818,184, filed May 1, 2013, which is incorporated by reference herein in its entirety.

TECHNICAL FIELD

This disclosure relates generally to devices, systems, and methods for the clinical evaluation of individual subjects e.g., and, more specifically, to identify acquired errors of metabolism and to identify appropriate metabolic supports to restore the biochemical functions within the body impacted by the error.

BACKGROUND

Metabolic pathways of healthy individuals have been thoroughly elucidated by the scientific community and full descriptions can be found in many biochemistry textbooks. It is well-established that each metabolic pathway is interconnected with other pathways. Each pathway requires an adequate supply of specific substrates, enzymes, co-factors and energy in order to function properly.

Research has shown that throughout an individuals' lifetime, metabolic pathways constantly change in response to external or internal stressors, including but not limited to pathogens, allergens, nutritional deficiencies, physical stress or injury, emotional stress, toxin exposure and buildup, overwork and lack of rest, etc. Further, genetically inherited familial weakness plays a significant role in how a body functions given the above listed stressors, as genes code for the enzymes that are specific catalysts responsible for the biochemical inter-conversions that sustain life, and can also pre-dispose an individual to weaknesses in biochemical pathways. If the stress is continuous, the metabolic network will adapt by biochemically re-routing through different pathways in an attempt to work around the weakness, but then the entire system becomes inefficient due to sub-optimal functioning of some biochemical pathways and compensatory over-functioning of others. These chronic changes may lead to symptoms and eventually produce disease.

A pathway in the metabolic network, by its very nature, affects other pathways. If a pathway is functioning too slowly, it will slow down the "production line", diminishing the downstream pathway activity and substrate production. At the same time, this creates a back log of inbound substrate that shifts to other pathways and alternate routes. Additionally, if a metabolic pathway is up-regulated and moving too fast, it can produce too much substrate and flood the pathways downstream with more than they can handle, again resulting in overflow alterations in the normal biochemical process.

Reasons for the metabolic network errors are varied and individual. A metabolic pathway can be functioning too slowly as the result of inhibited enzymes, inadequate supply of substrate or cofactors or a backlog from a downstream pathway not performing efficiently. A pathway can be functioning too fast as a result of enzyme up-regulation and an overproduction of biochemical substrates in an upstream pathway or over supplementation with nutrient cofactors.

Stress patterns, or acquired errors of metabolism, begin to manifest as symptoms when the body reaches a critical threshold of impairment. This phenomenon becomes most evident in areas of the body that tend to be genetically weak in an individual. Many common signs and symptoms of chronic health disorders are directly attributable to acquired errors of metabolism. In many cases, the dysfunctional pattern has become the "norm" with the body no longer attempting to correct the errors, but simply adapting to them. When this happens, the body is sufficiently stressed which provides little reserve for normal functioning. Any additional stress can push the body beyond its tolerance at which point symptoms and disease can develop.

Current Medical Standards of Care continue to diagnose and treat chronic diseases based on symptoms confirmed by the results of standard laboratory analyses and/or testing with a variety of medical devices. Knowledge of metabolic pathway errors has also allowed the pharmaceutical industry to create drugs that target specific pathways, or parts of pathways, as a means of alleviating symptoms, with the implication that the disease is under control when the symptoms are gone. Unfortunately, this approach to medicine is reactive, rather than proactive or preventative, and frequently does not resolve the acquired metabolic error causing the symptoms. Therefore, the disease is not truly under control as the metabolic imbalance may manifest itself as a recurrence of the same set of symptoms, or a new set of symptoms elsewhere in the body in the future.

For example, the mechanism of action for aspirin involves irreversible inhibition of the enzyme cyclooxygenase, suppressing the production of prostaglandins and thromboxanes, thereby reducing pain and inflammation. This is the intended effect of the aspirin on the enzyme, but the acquired metabolic error that produced excessive inflammation in the first place is not addressed by this treatment. If the cause of the metabolic imbalance is not resolved, inflammation will continue to be a health problem for this individual. Also of concern are the metabolic problems created by the use of medication and its impact on metabolic pathways. Although pharmaceuticals generally have the intended therapeutic effect, they often have secondary, undesirable side effects due to the adverse impact of the drug, either directly on unintended/untargeted metabolic pathways in the body or indirectly as the breakdown of the drug results in potentially toxic byproducts which the body must then eliminate. Much of the Physician's Desk Reference is devoted to such secondary, or side effects of pharmaceuticals.

In theory, non-traditional medical approaches to health care are more supportive of metabolic pathways than pharmaceutical-oriented medicine, and so should be helpful at relieving or resolving symptoms of chronic health problems. Similar to drug therapy, many nutritional programs are implemented based upon the symptoms exhibited by the patient (e.g., man or other animal, referred to as 'patient') at each office visit. Over the course of treatment however, it becomes exceedingly difficult to determine whether any true progress is being made in correcting the underlying metabolic weakness. Some non-traditional practitioners use additional laboratory evaluation to help determine specific interventions, which improves results. While this provides a general picture of deficiencies, it does not provide a road map to implement the therapeutic intervention and often results in over-supplementation. Similar to the concerns described above, over-supplementation can also cause stress to the biochemical pathways, by overwhelming them, and causing the overflow into untargeted pathways creating unintended side effects.

To be considered significant by practitioners in both the traditional and non-traditional medical communities, laboratory test results must be outside the normal reference range. To reach this level in the test, the metabolic imbalance must reach a serious degree of impairment. Important information about a patient's metabolic status can be obtained by looking at the patterns of metabolic markers observed within the laboratory test reports. Frequently, there are abnormalities observed in a given pathway based on the lab values, even when they are not out of the reference range. Evaluating only those results outside the reference range limits the practitioners' ability to correct a metabolic weakness earlier in the pathological process.

It is of particular note that most non-traditional approaches lack the specificity of process to methodically identify the order of the therapeutic interventions to properly target the biochemical/nutrient support necessary to achieve optimal results. The specific order will vary depending on the individuals' weaknesses in both genetic familial predisposition and individual exposures to stressors (e.g., viruses, bacteria, toxins, etc.).

A variety of Medical Devices are used within traditional and non-traditional medical approaches today and they provide information framed by each device's own unique technology. Common amongst these devices is that none can "diagnose" a patient's condition. Rather, the information provided by the device must be interpreted by a skilled specialist so that it can be added to other clinically relevant information, then used by the practitioner in developing a meaningful diagnosis, from which an appropriate treatment plan can be developed.

For example, sonograms, MRI scans, EEGs and EKGs are all FDA approved medical devices. Each provides informational output based upon its own unique technology. The informational output must then be interpreted by someone trained in reading this information so that it can be "framed" into a meaningful result. The device information or data is then used by a clinical practitioner, along with a variety of other information (e.g., physical exam, lab test results, patient interview, etc.) to formulate a diagnosis. It is important to note that though devices are routinely utilized in traditional medicine, many times they are misused, overused and/or misinterpreted, with occasional adverse impacts on the patient's overall prognosis.

Specific to the non-traditional medical device tools utilized, including bio-communication devices, electrical stimulation devices, cold lasers, and similar tools, some are registered with the FDA as Class 2 medical devices. And similar to traditional medicine, these tools are used, and occasionally misused and misinterpreted, by practitioners. Specific to bio-communication devices, data can be obtained by exposure to an electronic signature/signal. However the interpretation of the data must be properly interpreted to generate meaningful information. Many device manufacturers, and some end users, have made claims about the output from bio-communication devices that are not valid, and have subsequently given these devices a negative reputation, while calling to question the information they provide. Further, by incorrectly interpreting the information generated by these devices, some clinical practitioners place patients on many more nutrients and supplements than are necessary, which runs the risk of causing adverse stress to the metabolic network.

BRIEF SUMMARY

This disclosure is a clinical process method for the evaluation of an individual subject (e.g., man or other animal, referred to as 'patient') for acquired errors of metabolism using a bio-communication device that correlates laboratory test results, and identification of treatment of these errors in an ordered, sequential, targeted manner to achieve restoration of proper biochemical function and correction of the error. The method can be used to identify errors of metabolism through the acute or chronic stress patterns found in the biochemical pathways. Further, the method can guide the clinical practitioner in the application of metabolic interventions applied to the biochemical pathway(s) impacted for the correction of acquired errors of metabolism, which can then prevent the progression of symptoms to more serious disease states. The method uses a bio-communication screening protocol with comprehensive biochemical bio-surveys or libraries that is supported by laboratory testing as appropriate to the patient's unique needs. The results are compared and evaluated for patterns that indicate a problem in a particular metabolic pathway, or set of pathways.

This disclosure addresses the practice deficiency in most non-traditional approaches lacking specificity by imposing a structured order for the assessment of biochemical functions within the body, and subsequent metabolic interventions are prioritized, such that errors are addressed in a targeted, efficient and economical manner which—rather than overwhelming the body with too much supplementation/metabolite—provides the correct amount of support for the body at the appropriate time when the body needs it, so that the body can effectively repair the pathways. From this point, the body concurrently addresses two different issues, if and as it needs to. First, downstream and upstream biochemical pathways that were connected to the initial stress point often resolve once the first stress point is alleviated. Second, with this "most stressed" point in the pathway resolved, the body can then reveal errors in additional pathways that were either related to the initial error and require additional support/intervention to fully resolve, or be located in a completely different area of the biochemical network. Much like peeling back the layers of an onion, as one set of issues is resolved and "peeled away," any subsequent issues can then be exposed and addressed. An example of this would be poor digestion or unbalanced gut flora, which would impact many pathways because of lacking nutrients. Once these issues are addressed, with the digestive process functioning properly and gut flora brought back into balance, the associated stress resolves, leaving only those areas still under stress and in need of some type of support for resolution. By addressing the stressors in an ordered, methodical manner, the biochemical pathways that are truly the foundation of proper functioning are addressed first, and may reduce or eliminate the need for extra metabolites/nutrients as the body corrects its function naturally. This methodical approach recognizes that the body can indeed heal itself if provided the proper support in the proper order at the proper time. This disclosure enables the clinical practitioner to, on an individual basis, apply the method for assessment of an individual and in a structured, ordered manner introduce metabolic support to help their patient restore proper biochemical functioning, which very often permanently relieves symptoms, thereby halting and reversing the progression of the metabolic error to a disease state.

This disclosure utilizes bio-communication technology that correlates with laboratory data in the evaluation process, to identify stress on the body associated with these errors. In contrast to traditional uses of medical devices tools, when used properly, and within the context of this disclosure, these devices can become a significant assessment tool. By properly interpreting the information provided, and corroborating this information with laboratory measurements, the interpreted results can be very helpful at identifying the acquired errors of metabolism, enabling an intervention of targeted metabolic support, and ultimately resolving the symptoms and restoration of proper biochemical pathway functioning in the metabolic network. This subsequently reduces the symptoms associated with the metabolic errors, and halts the progression of the error toward the disease state.

Other advantages of the disclosure will become apparent from the following description in connection with the accompanying drawings, wherein is set forth by way of illustration and example, an embodiment of the present disclosure.

BRIEF DESCRIPTION OF THE DRAWINGS

FIG. 1 is a laboratory example of urea cycle markers.

DETAILED DESCRIPTION

Figure 2:
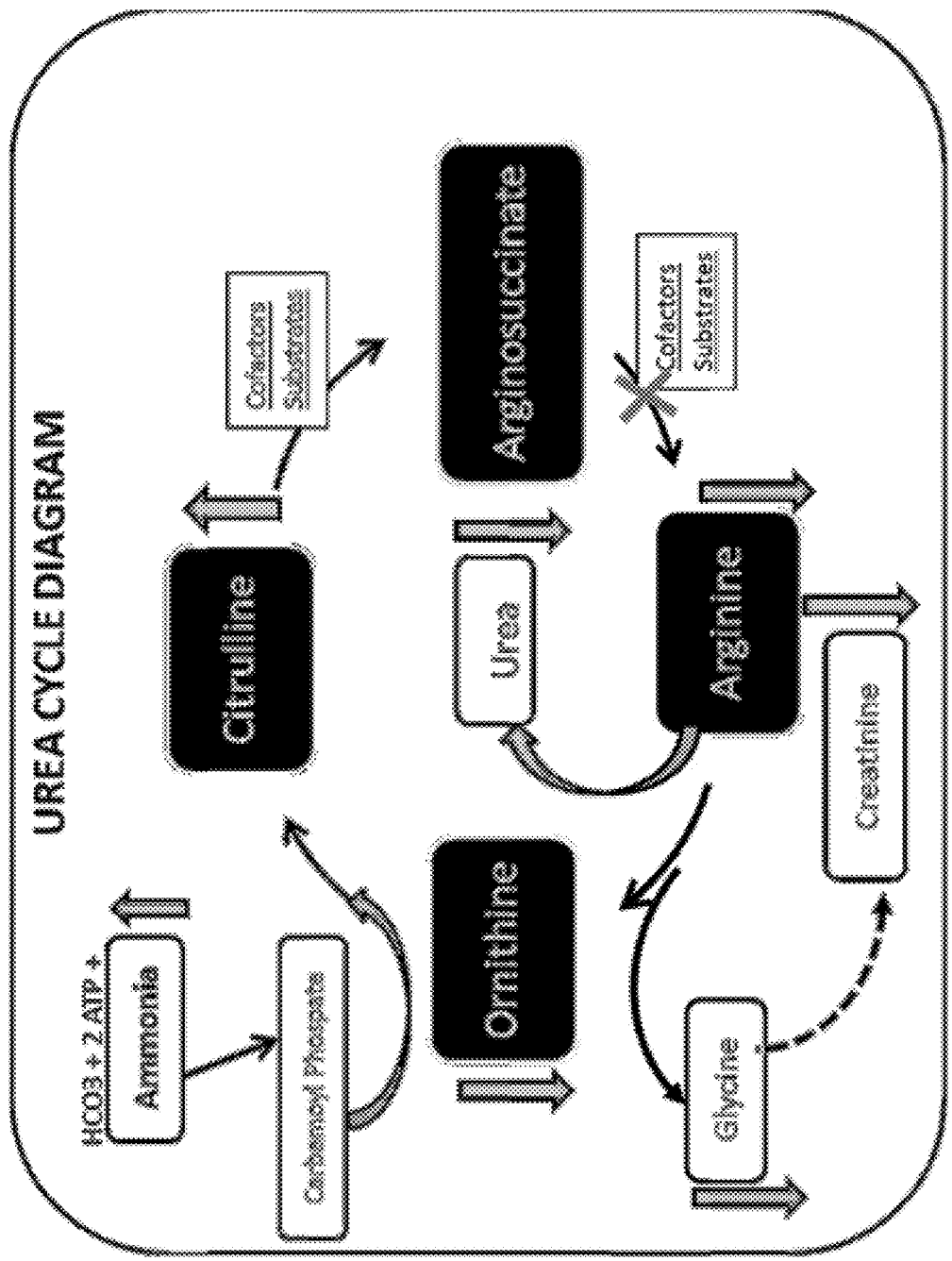
FIG. 2 is a diagram of a urea cycle with measurable shifts due to blockage.

As required, detailed embodiments of the present disclosure are disclosed herein. However, it is to be understood that the disclosed embodiments are merely exemplary and may be embodied in various forms. Therefore, specific structural and functional details disclosed herein are not to be interpreted as limiting, but merely as a basis for the claims and as a representative basis for teaching one skilled in the art of medicine to variously employ the present disclosure in virtually any appropriately detailed structure.

An embodiment of this disclosure comprises a clinical method to evaluate individual subjects (e.g., man or other animal, referred to as 'patient') for acquired errors of metabolism, identified within the biochemical pathways and to guide treatment interventions in an ordered, sequential, targeted manner for effective correction of the errors of metabolism. This results in the restoration of the impacted biochemical pathways to a proper functioning state, and resolution of acute or chronic symptoms. A patient's metabolic biochemical pathway network is evaluated by bio-communication protocol utilizing comprehensive biochemical bio-survey libraries that is supported by laboratory tests as appropriate. The disclosure imposes a structured, methodical format for the evaluation of the patient as well as an ordered prioritization for the interventions of metabolic support prescribed for treatment. By identifying the biochemical pathways involved, and the metabolic support useful to correct the error, the disclosure assigns a priority and an order resulting in a targeted intervention that provides appropriate metabolic support that respects the body's natural capability to heal. This targeted intervention subsequently corrects the errors within the metabolic network, which often halts the progression of symptoms to more serious disease states This disclosure is an ordered methodical process that guides a clinical practitioner through detailed evaluations to assist with formulation of appropriate diagnoses and determination of targeted interventions, while concurrently respecting the body's own natural capability to heal itself. By imposing a logically ordered evaluation process, and providing the specific supports the body requires (e.g., metabolites, nutrients, enzymes, etc.) when the body needs them, and allowing the body time to utilize the supports and formulate the correction, the disclosure provides both guidance and restraint to the clinical practitioner in the evaluation, diagnosis and treatment process. Loading and over loading patients with excessive numbers of supplements, with the idea of addressing every possible issue in a blanket approach, has been shown to be not only ineffective, but also inefficient as a treatment strategy. This disclosure's highly targeted and ordered method provides significant economies due to its efficient use of metabolic supports for the most effective means of resolving the error within the biochemical pathway.

TABLE 1

Components of the biochemical pathways associated with proteins, fats and carbohydrates and liver function All substrates, enzymes and cofactors in each of the metabolic pathways are able to be evaluated

| | |
|---|---|
| Protein Metabolism | Methionine Cycle |
| | Urea Cycle |
| | Transsulfuration |
| | Transamination |
| | Oxidative Deamination |
| | Amino Acid Synthesis Pathways |
| | Protein Synthesis Pathways |
| | Protein Degradation Pathways |
| Fat Metabolism | Lipolysis of Fats |
| | Fatty Acid Synthesis |
| | Fatty Acid Degradation |
| | B-Oxidation of fatty acids including Carnitine shuttle |
| | Fatty Acid Biosynthesis |
| | Fatty Acid Elongation |
| | Synthesis of ketone bodies |
| | Cholesterol and Steroid Metabolism |
| | Bile Acid and Bile Salt Synthesis |
| | Phospholipid Biosynthesis |
| | Sphingolipid Biosynthesis |
| | Eicosanoid Biosynthesis - Prostaglandins, Thromboxanes and Leukotrienes |
| Carbohydrate Metabolism | Glycolysis Pathway |
| | Gluconeogenesis and Glycogenesis Pathways |
| | Glycogenolysis Pathway |
| | Pentose/Hexose Phosphate Pathways |
| | Fructolysis Pathway |
| | Galactolysis Pathway |
| | Glycosylation Pathways |
| | Glycoprotein Synthesis |
| | Proteoglycans Synthesis |
| Liver Detoxification Pathways | Phase I |
| | Phase II |
| | Phase III |
| | Glutathione Synthesis |

Within this disclosure, the information generated from laboratory tests may be utilized in a different manner from the traditional assessment techniques currently being used in health care. While the generation of laboratory tests relies upon testing methods readily available at many clinical laboratories, it is in the interpretation and analysis of the lab values, when combined with the Bio-communication protocol, that support the evaluation method claimed in this disclosure. The primary laboratory tests utilized corroborate findings of the clinical evaluation method and support this disclosure are those that measure cellular energy metabolites, organic acids, amino acids, intermediary metabolites and oxidative stress markers, though other tests may be added as appropriate for the patient's specific situation and their unique presentation of symptoms. Unlike the customary analysis of the test results utilized in traditional medicine, the exact amount of a substance found in the test sample is only a portion of what is evaluated. To this, the relative differences of substrates, which may be within the normal reference range, are also interpreted and may indicate a reduction or blockage in the flow of the pathway. For example, Substrate A may be in a high normal range, while Substrate B and Substrate C may be in low normal ranges. All can be within the specified acceptable reference ranges for the individual substrate, and yet when taken as a whole indicate a need for metabolic support, such as a lacking nutrient.

For example the lab results seen in FIG. 1 represent a blockage in the urea cycle. The blockage occurs most likely between the conversion of Citrulline and Arginine which results in decreased production of urea and buildup of ammonia. Units of measure for the reference range: micromole/gm creatinine except for ammonia which is mmol/gm creatinine.

Additionally, as seen in TABLE 1 and FIG. 2, the lack of efficient flow of the pathway which can be helpful to the practitioner in determining an appropriate targeted nutrient to support and correct the error. In this example, this biochemical pathway diagram begins with ammonia combining with bicarbonate and ATP's to form Carbamoyl Phosphate which then enters the Urea Cycle (the path to eliminate ammonia). Ammonia and Citrulline are elevated. Between Citrulline and Arginine there is a blockage/inefficiency that is demonstrated in the lab and diagram. Arginosuccinate was not measured in the lab results so the blockage could be before or after it. The upward arrows indicate and elevated value (Ammonia & Citrulline) and the downward arrows indicate a reduced value. In this case, all downstream metabolites beyond the blockage are reduced. With implementations of this disclosure, we can select from a number of metabolic interventions, such as cofactor or substrates, to support these points and look for which substances best supports/balances the pathway so that the pathway functionality is restored, and the body regains the ability to eliminate ammonia as Urea. The other impact of the dysfunction of the urea cycle is the low level of creatinine which would likely manifest as low muscle mass. Due to the complexity of the biochemical network, it is not feasible to include the many detailed possibilities of support within this diagram.

Figure 3:
FIG. 3 is a sample biological survey.

As elucidated by the scientific community and fully described in many physiology and biochemistry textbooks, it is well known that every cell in the body is networked together, and constantly sending and receiving information energetically to coordinate the millions of functions in the body. This inter-cellular communication can be altered in response to stressors such as pathogens, allergens or pollution. When the body is no longer able to effectively handle the stress, symptoms develop accompanied by changes in the body's biochemical function. Bio-communication refers to any clinical method that assesses the body's response to resonant signals, applied in various forms by various devices which use technologies such as non-ionizing, non-thermal, low energy, frequency specific electromagnetic radiation or low voltage alternating or direct current, to the body. These devices can simulate pre-selected stimuli or stressors in order to obtain information about the current health status of a patient. The comprehensive list, or bio-survey, shown in TABLE 2 and FIG. 3, for example, is a library of possible stressor points in this disclosure, and can be implemented on FDA approved commercially available bio-communication devices capable of exchanging information between a computer and a patient's body.

TABLE 2

Figure 4:
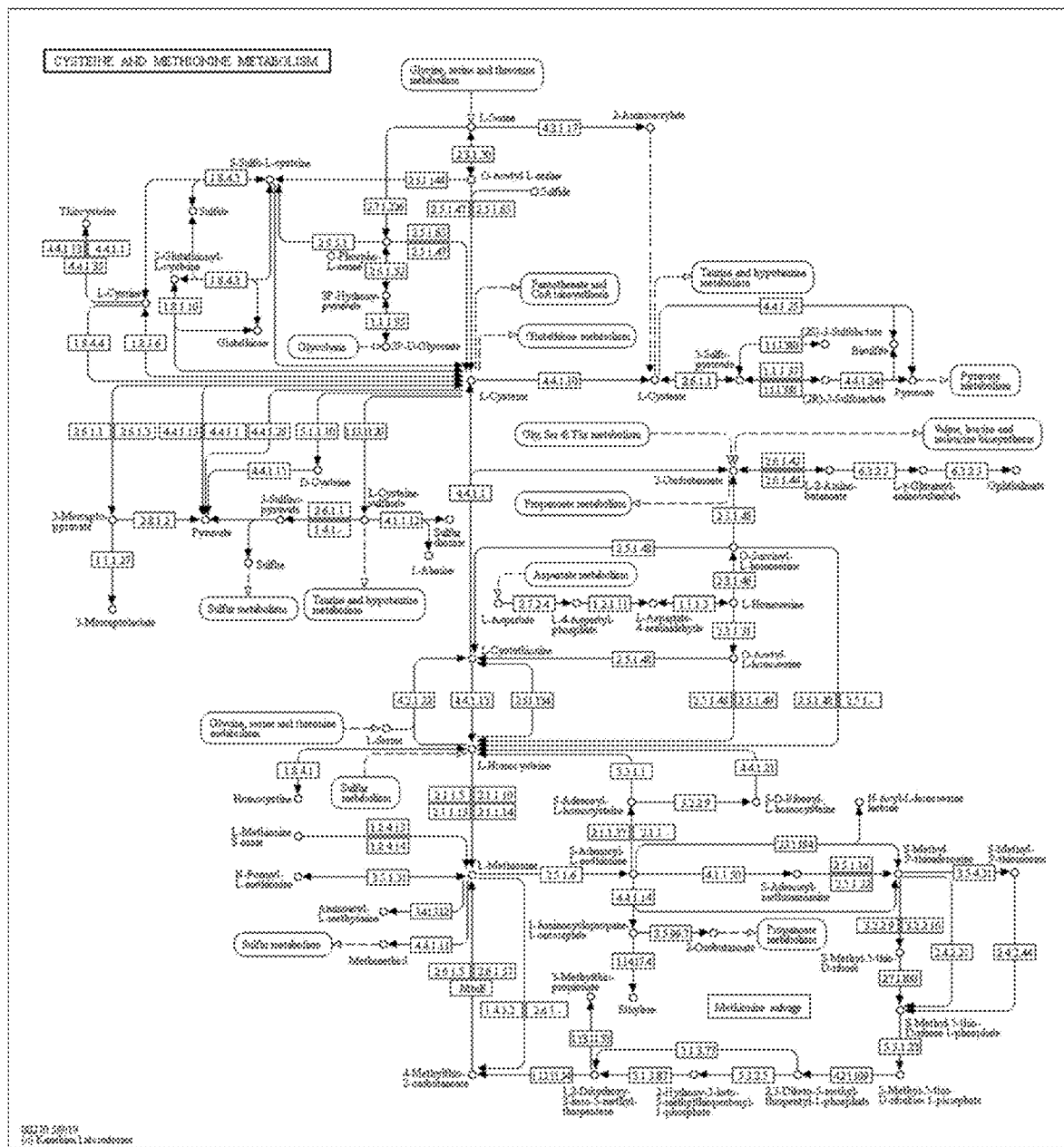
FIG. 4 is a diagram of the KEGG Pathway, including the Methionine Cycle.

Example of Biochemical library inclusive to connecting points of other pathways - Methionine Cycle Library 5-Methyltetrahydrofolate
Adenosine
Adenosine 5-triphosphate (ATP)
Adenosylhomocysteinase
Adenosylhomocysteine Hydroxylase
Betaine
Betaine aldehyde
Betaine aldehyde dehydrogenase
Betaine-homocysteine methyltransferase
Choline
Choline dehydrogenase
Creatine
Dimethylglycine
Dimethylglycine dehydrogenase
Diphosphate
Folate
Glutamate
Glycine
Glycine methyltransferase
Guanidoacetate
Guanidoacetate methyltransferase
Homocysteine
Homocysteine S-methytransferase
Magnesium
Methionine
Methionine adenosyltransferase
Methionine synthase
Methyl group
Methylcobalamin (Vit B12)
Methylglycine (sarcosine)
Methylglycine dehydrogenase
Niacin (Vit B3)
Nicotinamide adenine dinucleotide phosphate (NADP)
Orthophosphate
Phosphate (PO4)
Pyridoxal-5-phospate (Vit B6)
Pyrophosphate
Riboflavin (Vit B2)
S-Adenosylhomocysteine
S-Adenosylmethionine
Tetrahydrofolate
Trimethylglycine
Water/H2O As referenced in TABLES 1 and 2 and as can be seen in FIG. 4, the Methionine Cycle, commonly referred to as methylation, is a biochemical pathway associated with proteins. Methionine is a sulfur-containing amino acid that enters the body through dietary proteins, is used in forming proteins in the body, and is the precursor (through the methionine cycle) of the sulfur-containing amino acids homocysteine, cysteine, and taurine.

This disclosure incorporates the use of a bio-communication protocol. It uses a device similar to an ECG, or an EEG to record the electrical activity on the skin to evaluate the activity of the heart and brain. Other device-based tests measure the body's response to electrical stimuli e.g. nerve conduction study. A bio-communication device utilizes its technology to measure a patient's response to a comprehensive list or library, sometimes referred to as a bio-survey. This may include the substrates, enzymes, co-enzymes, cofactors and energy (e.g. ATP) in certain metabolic biochemical pathways in order to identify metabolic imbalances within broad categories, including but not limited to: metabolism involving carbohydrates, lipids, proteins, biosynthetic pathways and liver detoxification pathways. From the bio-survey, a clinical practitioner trained in the interpretation of the information generated can identify metabolic deficiencies, which become readily apparent in the assessment readings generated. The information generated from the bio-communication device and protocol can, when added to other evaluation protocols (e.g., physical exam, patient interview, etc.), guide the clinical practitioner in developing a therapeutic plan by measuring the physiologic response of the body to various metabolic supports, enabling the clinical practitioner to identify any potentially helpful supports as well as those that are not helpful, and developing a targeted treatment plan for the individual.

The resonant signal, biological response or stress technology, used within bio-communication protocols is also known as bio-energetic feedback, electro-dermal screening (EDS) or electro-acupuncture according to Voll (EAV). This technology uses a device, usually a hand cradle or ohmmeter with stylus, to send the body a subtle, computer-generated impulse or digital signature representing physical stimuli such as drugs, nutrients, toxins, foods, or other physical stress. A proprietary entanglement process called linking is used to associate the physical stimuli with the digital code created by the computer allowing the computer software to be able to communicate with the body. The device converts the information from digital to analog and vice versa to facilitate the communication process between the body and the computer.

Each digital signature elicits a physiological response from the body which is reflected as a change in the electrical conductivity of the skin known as a galvanic skin response (GSR). GSR technology is well-established and devices implementing this technology are generally registered with the FDA as Class II medical devices. Fluctuations in skin conductivity or GSR are measured by a bio-communication device and sent back to the computer for analysis and interpretation. The data received from the device is plotted and analyzed for coherence, which is defined as a state where two or more things exist without conflict. To determine whether there is coherence, the device begins by measuring a baseline value for the energy of the skin prior to sending stimuli to the body. Then the computer calculates deviations from the baseline or from coherence as the body responds to each digital signature.

After analyzing the data, the computer software displays the data in a graphical format, ranking the body's response from high to low. Current applications of bio-communication medical devices primarily focus upon determining which organ systems or meridians are imbalanced and/or which medicinal or nutritional products will be the most effective in restoring the balance.

The present disclosure utilizes the existing bio-communication technology in a far more detailed manner to assess acquired errors within the biochemical pathways. The device manufacturers refer to errors as imbalances or stressors. This use within the disclosure has led to the creation of useful libraries and bio-surveys containing comprehensive lists of components in the biochemical pathways including but not limited to carbohydrate, lipid, protein metabolism and liver detoxification pathways. These are unique to this disclosure. See FIG. 2. This new use of an existing medical device can provide a clinical practitioner with information about the health of the body through an evaluation of its many functions, including but not limited to its ability to process proteins, carbohydrates and fats/lipids, which are fundamental functions of the body, as well as proper liver function and detoxification. By correctly interpreting the information generated by the bio-survey and libraries, the practitioner will have data that, when paired with other information (e.g., physical exam, lab test results, patient interview, etc.), becomes the basis for the generation of an appropriate diagnosis of the patient, and to use the device libraries to identify appropriate interventions in the development of a meaningful targeted therapy/treatment plan to resolve the issues and facilitate the restoration of proper biochemical pathway functioning, which subsequently alleviates symptoms and enables the patient to obtain improved physical health.

It is of particular note that most non-traditional approaches lack the specificity of a process to methodically identify the order of the therapeutic interventions to properly target the biochemical/nutrient support necessary to achieve optimal results. That specific order will vary depending on the individuals' weaknesses in both genetic familial predisposition and individual exposures to stressors (e.g., viruses, bacteria, toxins, etc.). This disclosure addresses this practice deficiency by imposing a structured order for the assessment of biochemical functions within the body, and prioritizing subsequent metabolic interventions, such that errors are addressed in a targeted, efficient and economical manner which—rather than overwhelming the body with too much supplementation/metabolite—provides the correct amount of support for the body at the appropriate time when the body needs it, so that the body can effectively repair the pathways. First, downstream and upstream biochemical pathways that were associated with the initial stress point often resolve once the first stress point is alleviated. Second, with the "most stressed" point in the pathway resolved, the body can then reveal errors in additional pathways that were either related to the initial error and require additional support/intervention to fully resolve, or be located in a completely different area of the biochemical network. Much like peeling back the layers of an onion, as one set of issues is resolved and "peeled away," any subsequent issues can then be exposed and addressed. An example of this would be poor digestion or unbalanced gut flora, which would impact many pathways because of lacking nutrients. Once these issues are addressed, with the digestive process functioning properly and gut flora brought back into balance, then associated stress resolves, revealing those areas still under stress and in need of some type of support for resolution. By addressing the stressors in an ordered, process method manner, the biochemical pathways that are truly the foundation of proper functioning are addressed first, and may reduce or eliminate the need for extra metabolites/nutrients as the body corrects its function naturally. This methodical ordered approach recognizes that the physical organism, the human body, can indeed heal itself if provided the proper support in the proper order at the proper time. This disclosure enables the clinical practitioner to, on an individual basis, apply the method for assessment of an individual and in a structured, ordered manner introduce metabolic support to help their patient restore proper biochemical functioning, which very often permanently relieves symptoms, thereby halting and reversing the progression of the metabolic error to a disease state.

As previously stated, most chronic health disorders are the result of multiple poorly regulated or obstructed metabolic pathways. When the body's metabolic pathways are strained at multiple points, they are incapable of utilizing the full spectrum of nutrients available to them, either through diet or through supplementation. Therefore, it is useful to address fundamental metabolic imbalances as soon as possible in the assessment of an individual. With this in mind, the present disclosure provides a precise sequential order in which to evaluate an individual, targeted at specific biochemical pathways. We refer to this as a "Foundational Approach" because it is supporting the very foundations on which living organisms are built and need to function. When these biochemical pathways work properly, restoration of proper functioning can occur. This disclosure, with the structured approach to evaluations and the prioritization of appropriate metabolic interventions, is implemented in a prescribed order to achieve the best clinical results. Regardless of the number or magnitude of acquired errors of metabolism identified during the evaluation process, or the type or severity of symptoms exhibited, patients are treated for metabolic pathway imbalances found in the broad metabolic categories (e.g. carbohydrate, fat and protein, liver detoxification) simultaneously. However, pathway imbalances within each of these metabolic categories are treated in a specific order to best achieve success.

The order of priority for interventions depends upon the pathways involved in the error of metabolism. With elimination or degradation pathways, it is useful to start at the end of the pathway, to ensure the pathway is unobstructed and open in order to eliminate output or wastes before you support areas toward the beginning of the pathway, which will generate more output or wastes. For instance, with protein degradation it can be essential that the urea cycle be supported initially, since the urea cycle enables the body to eliminate ammonia, and ammonia levels rise if the urea cycle is not working properly. Ammonia is toxic to the body in high amounts, so build-up of this waste product can have significant adverse impact on the body. When dealing with fats and carbohydrates, it is useful to support the breakdown of these components from the largest molecule to the simplest so that the simple substrates are available for biosynthesis pathways. If fats aren't broken down to the smallest components (e.g., fatty acid degradation), then the downstream biosynthetic pathways involving the immune system, fat soluble vitamin production, hormone production, energy production, etc., will lack the substrates to function properly. When dealing with a bio-synthesis pathway, it is useful to start at the beginning. So, as these examples demonstrate, it is the recognition of the body's natural processes that provide and guide the evaluation and treatment process of the clinical practitioner. Rather than fight the natural process, it is the purpose of this disclosure to impose an order of evaluation that guides the clinical practitioner to make an appropriate diagnosis, then determine the appropriate intervention, which ultimately determines the effectiveness and tolerability of this disclosure in prescribing appropriate metabolic supports to the body so that it can do the important work of restoring proper metabolic functioning. If the exact evaluation process methodology sequence described in this disclosure is followed, it is possible to adequately support an impaired metabolic pathway without causing secondary stress on either upstream or downstream pathways. Clinical use has found this disclosure's targeted order of evaluation and treatment interventions to be considerably more effective at supporting the body's biochemical pathways appropriately, which resolves the difficult health problems that other approaches currently use within the traditional and non- traditional medical communities. Additionally, and of note, this disclosure's ordered methodology has shown that while targeted metabolic support (e.g., nutrients, supplements, etc.) is often implemented, it routinely consists of fewer nutrients at smaller doses than previously utilized. This leads to a safer, more effective treatment plan that is easier to implement and manage for the patient with fewer side effects.

Using this disclosure, a patient is evaluated in a systematic manner. The order of biochemical pathway evaluation and treatment is useful to avoid buildup of toxic metabolites (waste products) and to avoid creating undo stress on unsupported pathways. As errors of metabolism are revealed, and appropriate support is identified and provided to the body, the targeted approach enables the body to make correction to the pathway function. Support interventions could consist of dietary modifications, nutrient supplements, homeopathic remedies, botanicals, enzymes, energetic treatments, acupuncture, other therapeutic intervention, etc. There are specific supports used at each stage of the evaluation process, as dictated by the biochemical pathways impacted by the error of metabolism, which results in an individualized treatment plan. As the evaluation methodology progresses, the specific therapeutic regimen will change and evolve as the body restores proper functioning of the biochemical pathways. Metabolic pathways that previously needed support to correct their functioning will, over time, have a reduced need for support. Ultimately the biochemical network is fully restored to proper functioning and will require limited support. In the final phase of the evaluation methodology and treatment protocol, very little nutritional support is required. This is referred to as a "maintenance program." The evaluation methodology recognizes that due to familial genetic inheritance patterns, a maintenance program may be useful to provide continued support for the metabolic pathways that are inherently weak. By maintaining support for these "weak points" within the biochemical pathway network, the patient can then prevent the progression of simple metabolic imbalances that, left alone would progress towards symptoms and development of disease.

When compared to other approaches in health care, this disclosure methodology provides a specific and targeted evaluation process, enabling licensed clinical practitioners to formulate diagnoses with increased accuracy, and to determine effective treatment interventions as opposed to the "trial and error" and mass support approaches used currently. These interventions are also simpler to implement and can reduce stress on the patients, and are individualized, recognizing that our genetic makeup and weaknesses are inherently unique. When applied correctly, this disclosure process can be more therapeutically effective for the patient because only metabolic supports that are known to resolve the error within the biochemical pathway, or feeder pathways, are recommended, which is more efficient as fewer metabolic supports, at lower doses, are typically used. This method is more affordable and cost efficient, because the targeted nature of the treatment is focused on full resolution of the biochemical issue, resulting in a faster rate of symptom resolution and improvement in metabolic functioning. See the following case study.

Case Study—Clinical Example—Old And New Approach Used In Same Patient

Presentation: 45 year old female presented with episodic vertigo, migraine headaches, acne, chronic sinus congestion, fatigue, joint pain and possible food allergies.

Review of Systems was positive for hearing loss, neck pain, tinnitus with aspirin use, constipation, daily headaches, sinus pressure which increases with barometric pressure changes, teeth pain, sensitivity to perfumes which set off migraines, difficulty losing weight, improved symptoms with removing gluten, casein and soy from her diet, peeling dry skin on feet and toenail fungus.

Past Medical History was significant for two sinus surgeries, Meniere's Diseases, Multinodular Goiter, liver cysts, Gastroesophageal Reflux Disease, post-partum depression, varicose veins, horrible acne since birth of her 4th child, decreased exercise tolerance, palpitations, and Pre-eclampsia with her 3rd pregnancy.

Family History was significant on the maternal side for colon cancer (g-ma and aunt), grandpa died young with a heart attack, lung cancer (3 relatives—all smokers), an aunt died with Hodgkins Lymphoma, mom with early Alzheimer's Disease, sister with Systemic Lupus Erythematosis, another sister died in childhood of Acute Lymphocytic Leukemia. Paternal side was significant for coronary artery disease, hypercholesterolemia, strokes and vascular disease. Five paternal cousins diagnosed with various cancers—breast (2)—four are deceased. She has four children, her eldest daughter has clinical depression and food allergies, 2nd son had Kawasaki's Disease at 10 months and delayed speech, 4th child had PDD-NOS (autism). To sum it up, lots of cancer on one side and lots of coronary/vascular disease on the other side.

Physical Exam is significant for moderately severe acne on face and back with scarring, maxillary sinus tenderness and roughness of skin on posterior upper arms. Remainder of exam was unremarkable.

Labs: (urea, transsulfuration, methionine cycle and folate abnormalities seen) dysbiosis markers were present.

Stool: Protein fibers and low chymotrypsin level, high cholesterol content with low phospholipid levels, low pH, abnormal flora with no growth of lactobacillus and suboptimal bifidobacterium, 4+growth of 2 strep species, 3+staph aureus, 3+Klebsiella Pneumoniae, 2+Candida albicans and 2+Rhodoturula species. Eosinophilic Protein X was elevated.

Urine: Elevated levels of Arabinose, Citramalic Acid, DHPPA, alpha Ketoglutaric Aicd, Adipic Acid, Suberic Acid, Homovanillic Acid, Formiminoglutamic Acid, Methylmalonic Acid, Kynurenic Acid, Urea, Ammonia, Glutamic Acid, Aspartic Acid, Sarcosine, 8-OHdG, Cysteine, alpha-Aminoadipic Acid. There were low levels of Lysine, Glycine, Arginine, Citrulline, Glutamine, Cystine, Cystathionine, alpha-Amino-N-butyric Acid Blood-Bicarbonate level -19. Low total protein and HDL—normal total cholesterol level, borderline anemia with low ferritin level. Chemistries were otherwise normal including thyroid function testing despite Multinodular goiter.

Bio communication Device Protocol Evaluation—The bio-communication protocol evaluation available at the time of the initial presentation was not able to evaluate biochemical pathways, as the libraries to support this level of evaluation with this type of device had not yet been developed and built.

Treatment Approach:

Initial: Based on history, symptoms, physical and labs only

Based on the clinical evaluation and laboratory evaluation, the patient demonstrated a need for support of methionine cycle, folate pathway, transsulfuration, urea cycle, and carbohydrate metabolism. She was placed on digestive enzymes, probiotics, and support for methionine and folate pathways using high dose methyl B12 and 5-MTHF. She felt improved for about 3 weeks but then began to feel worse again. She abandoned the program after 3 months when her symptoms did not improve.

1 year later: Based on history, symptoms, physical and labs, with addition of using the disclosed methodology.

The patient returned to the clinic with the same complaints and was re-evaluated with the disclosure, the evaluation methodology that had been developed and built to evaluate the functioning of the biochemical pathways which had not previously been available. She demonstrated stress with Methionine cycle, Folate pathway, Transsulfuration, Urea Cycle, and Glycolysis which had previously been demonstrated via laboratory evaluation. Digestion of Carbohydrates, Fats and Proteins was also stressed. Once again she was placed on digestive enzymes and probiotics to support her digestive stress. The Urea Cycle and Glycolysis were supported first this time using nutrients which supported these pathways. Her symptoms began to improve. At each follow up visit, support was added to the program based upon the evaluation of errors within the metabolic pathways targeted to support the evolving restoration of proper biochemical pathway function. She continued to improve and after 4 months her biochemical stress patterns were evaluated and found to be balanced and stable. Her symptoms of migraine headaches, acne, chronic sinus congestion, fatigue, constipation and joint pain were no longer problematic.

In this example, the patient had poor results with the initial treatment even though the clinical and laboratory evaluation indicated a need for the nutrients. When the initial program was undertaken, it supported the methionine cycle and folate pathway without regard to stressed downstream pathways of transsulfuration and the urea cycle which were already not functioning properly. Given the interrelated nature of the network of biochemical pathways, it makes sense that she felt better transiently, but then began to feel worse again as the downstream pathways became overwhelmed and even more stressed. It was a "band aid" approach that ultimately failed to achieve the desired effect.

When we changed the approach to our evaluation process, imposing an order of priority that recognized and respected the natural functions of the body, and subsequently prioritized the metabolic support such that the protein degradation (urea cycle) was addressed first to alleviate the toxic buildup of ammonia within the body, the results were much improved for this patient. This disclosure methodology enabled the evaluation process to target support interventions to enable the body to restore the proper biochemical pathway function, resolving errors while alleviating symptoms to achieve a stable and balanced biochemical pattern. Today this patient no longer requires nutrient support, she continues to be symptom free and the evaluation methodology continues to show her biochemical pathways are balanced and stable.

The invention claimed is:

1. A method for treating a metabolic network of a patient, the method comprising:
   establishing a metabolic baseline of fundamental biochemical pathways of the patient by measuring, using a bio-communication device, a baseline value of fundamental biochemical pathways in a body of the patient without stimuli or stressors not generated by the bio-communication device;
   testing the metabolic baseline by simulating, with the bio-communication device, one or more pre-selected stimuli or stressors, which cause a response in the patient that is indicative of a health status of the fundamental biochemical pathways of the patient, from a library of one or more stimuli or stressors and measuring, with the bio-communication device, the response of the patient to the one or more pre-selected stimuli or stressors;
   generating, with the bio-communication device, an assessment reading corresponding to the metabolic baseline and the response of the patient to the one or more pre-selected stimuli or stressors that have been simulated;

identifying one or more metabolic dysfunctions in the metabolic baseline by comparing, with bio-communication software, the response of the patient to the one or more pre-selected stimuli or stressors that have been simulated to the metabolic baseline;

determining that the patient has a dysfunctional fundamental biochemical pathway based on the one or more metabolic dysfunctions that have been identified and one or more evaluation protocols;

assessing a metabolic treatment plan for correcting the one or more metabolic dysfunctions by simulating, with the bio-communication device, one or more metabolic supports or support interventions from a library of one or more metabolic supports or support interventions, wherein each of the metabolic supports or support interventions facilitate restoration of proper fundamental biochemical pathway functioning, and measuring, with the bio-communication device, the response of the patient to the one or more metabolic supports or support interventions that have been simulated;

developing a prescribed metabolic treatment plan by adding, based on the assessment, one or more metabolic supports or support interventions to the prescribed metabolic treatment plan if the response of the patient to the one or more metabolic supports or support interventions that have been simulated indicates restoration of proper fundamental biochemical pathway functioning to the dysfunctional fundamental biochemical pathway and refraining from adding, based on the assessment, the one or more metabolic supports or support interventions to the prescribed metabolic treatment plan if the response of the patient to the one or more metabolic supports or support interventions that have been simulated does not indicate restoration of proper fundamental biochemical pathway functioning to the dysfunctional fundamental biochemical pathway; and implementing the prescribed metabolic treatment plan to support the dysfunctional fundamental biochemical pathway of the patient to restoration of proper functioning.

2. The method of claim 1, wherein the bio-communication device uses an electrodermal test to measure one or more of the metabolic baseline of the fundamental biochemical pathways in the body of the patient without the stimuli or stressors not generated by the bio-communication device, the response of the patient to the stimuli or stressors, and the response of the patient to the one or more metabolic supports or support interventions that have been simulated.

3. The method of claim 1, wherein the one or more evaluation protocols comprises one or more of a physical exam of the patient, a patient interview, or a lab test.

4. The method of claim 1, wherein the metabolic baseline comprises one or more of protein metabolism, fat metabolism, carbohydrate metabolism, urea cycle, transsulfuration, and liver detoxification pathways or pathways connected thereto.

5. The method of claim 1, wherein the library of one or more stimuli or stressors includes one or more of pathogens, allergens, nutritional deficiencies, physical stress or injury, emotional stress, pollution, toxin exposure and buildup, overwork and lack of rest, viruses, bacteria, and toxins.

6. The method of claim 1, wherein the library of one or more metabolic supports or support interventions comprises one or more of dietary modifications, nutrient supplements, homeopathic remedies, botanicals, enzymes, energetic treatments, or acupuncture points.

7. The method of claim 1, wherein the metabolic treatment plan further comprises a metabolic treatment plan period and wherein the metabolic treatment plan period includes time for the patient to administer the one or more metabolic supports or support interventions in the prescribed metabolic treatment plan and for the body of the patient to restore the fundamental biochemical pathways.

8. The method of claim 7, wherein the method further comprises:

awaiting expiration of the metabolic treatment plan period;

retesting the metabolic baseline after the metabolic treatment plan period to re-evaluate the health status of the fundamental biochemical pathways of the patient by simulating, with the bio-communication device, one or more pre-selected stimuli or stressors, which cause a response in the patient that is indicative of the health status of the fundamental biochemical pathways of the patient, from a library of one or more stimuli or stressors and remeasuring, with the bio-communication device, the response of the patient to the one or more pre-selected stimuli or stressors that have been simulated;

generating, with the bio-communication device, a reassessment reading corresponding to the metabolic baseline and the response of the patient to the one or more pre-selected stimuli or stressors that have been simulated from retesting the metabolic baseline;

reidentifying one or more metabolic dysfunctions in the metabolic baseline by comparing, with the bio-communication software, the response of the patient to the one or more pre-selected stimuli or stressors that have been simulated from retesting the metabolic baseline to the metabolic baseline;

re-determining that the patient has the dysfunctional fundamental biochemical pathway based on the one or more metabolic dysfunctions that have been reidentified and the one or more evaluation protocols;

assessing a modified metabolic treatment plan for correcting the one or more metabolic dysfunctions that have been reidentified by simulating, with the bio-communication device, one or more metabolic supports or support interventions from the library of one or more metabolic supports or support interventions, wherein each of the metabolic supports or support interventions facilitate restoration of proper fundamental biochemical pathway functioning, and measuring, with the bio-communication device, the response of the patient to the one or more metabolic supports or support interventions that have been simulated, wherein the modified metabolic treatment plan is different from the prescribed metabolic treatment plan;

developing a modified prescribed metabolic treatment plan by adding, based on the reassessment, the one or more metabolic supports or support interventions to the modified prescribed metabolic treatment plan if the response of the patient to the one or more metabolic supports or support interventions that have been simulated indicates restoration of proper fundamental biochemical pathway functioning to the dysfunctional fundamental biochemical pathway and refraining from adding, based on the reassessment, the one or more metabolic supports or support interventions to the modified prescribed metabolic treatment plan if the response of the patient to the one or more metabolic supports or support interventions that have been simulated does not indicate restoration of proper fundamental biochemical pathway functioning to the dysfunctional fundamental biochemical pathway; and implementing the modified prescribed metabolic treatment plan to support the dysfunctional fundamental biochemical pathway of the patient to restoration of proper functioning.

9. The method of claim 1, wherein the prescribed metabolic treatment plan includes one or more metabolic supports or support interventions corresponding to a first dysfunctional fundamental biochemical pathway, the method further comprising, after proper functioning of the first dysfunctional fundamental biochemical pathway has been restored, providing a supplemental metabolic treatment plan that includes one or more metabolic supports or support interventions for a second dysfunctional fundamental biochemical pathway.

10. The method of claim 9, wherein a deficiency in the first dysfunctional fundamental biochemical pathway is greater than the deficiency in the second dysfunctional fundamental biochemical pathway.

11. The method of claim 1, wherein, if the dysfunctional fundamental biochemical pathway is an elimination or degradation pathway, the prescribed metabolic treatment plan includes one or more metabolic supports or support interventions for restoring elements toward an end of the dysfunctional fundamental biochemical pathway, and if the dysfunctional fundamental biochemical pathway is a biosynthesis pathway, the prescribed metabolic treatment plan includes one or more metabolic supports or support interventions for restoring elements toward a beginning of the dysfunctional fundamental biochemical pathway.

12. The method of claim 1, wherein providing the prescribed metabolic treatment plan includes providing a metabolic maintenance plan for maintaining proper functioning of one or more previously treated dysfunctional fundamental biochemical pathways.

13. The method of claim 1, wherein the prescribed metabolic treatment plan includes one or more metabolic supports or support interventions for simultaneously treating each dysfunctional fundamental biochemical pathway.

\* \* \* \* \*